United States Patent
Vendely et al.

(10) Patent No.: US 10,478,280 B2
(45) Date of Patent: Nov. 19, 2019

(54) METHODS AND DEVICES FOR DELIVERING AND SECURING ADJUNCT MATERIALS TO A TREATMENT SITE

(71) Applicant: Ethicon LLC, Guaynabo, PR (US)

(72) Inventors: Michael J. Vendely, Lebanon, OH (US); Charles J. Scheib, Loveland, OH (US); Susanne Landgrebe, Sulfeld (DE); Frederick E. Shelton, IV, Hillsboro, OH (US); Susan Cooper, Cincinnati, OH (US); Dennis D. Jamiolkowski, Long Valley, NJ (US)

(73) Assignee: Ethicon LLC, Guaynabo, PR (US)

( * ) Notice: Subject to any disclaimer, the term of this patent is extended or adjusted under 35 U.S.C. 154(b) by 119 days.

(21) Appl. No.: 15/435,955

(22) Filed: Feb. 17, 2017

(65) Prior Publication Data

US 2018/0235591 A1    Aug. 23, 2018

(51) Int. Cl.
| | |
|---|---|
| *A61B 17/08* | (2006.01) |
| *A61D 1/00* | (2006.01) |
| *A61F 2/00* | (2006.01) |
| *A61B 17/29* | (2006.01) |
| *A61B 17/072* | (2006.01) |

(Continued)

(52) U.S. Cl.
CPC ...... *A61F 2/0063* (2013.01); *A61B 17/07207* (2013.01); *A61B 17/07292* (2013.01); *A61B 17/29* (2013.01); *A61B 2017/005* (2013.01); *A61F 2002/0072* (2013.01); *A61M 35/003* (2013.01)

(58) Field of Classification Search
CPC ............ A61B 17/00491; A61B 17/068; A61B 17/07207; A61B 17/07292; A61B 2017/005; A61F 2/0063
USPC ........................................ 606/213, 214, 219
See application file for complete search history.

(56) References Cited

U.S. PATENT DOCUMENTS

| | | |
|---|---|---|
| 7,143,925 B2 | 12/2006 | Shelton, IV et al. |
| 7,601,118 B2 | 10/2009 | Smith et al. |
| 8,317,070 B2 | 11/2012 | Hueil et al. |

(Continued)

FOREIGN PATENT DOCUMENTS

| | | |
|---|---|---|
| EP | 2090252 A2 | 8/2009 |
| EP | 2644126 A2 | 10/2013 |

(Continued)

OTHER PUBLICATIONS

Extended European Search Report for EP App. No. 18157213.2 dated Aug. 14, 2018 (10 pages).

*Primary Examiner* — Melanie R Tyson
(74) *Attorney, Agent, or Firm* — Mintz Levin Cohn Ferris Glovsky and Popeo, P.C.

(57) ABSTRACT

Devices and methods for placing an adjunct at a tissue treatment site prior to delivering staples through the tissue and adjunct are provided. In one embodiment, a flowable adjunct precursor can be deposited on the surface of the tissue at the tissue treatment site. The flowable adjunct precursor can be configured to solidify after deposition to form an adjunct. In another embodiment, an adjunct delivery device can include a non-stapling end effector configured to deliver an adjunct to a tissue treatment site. In either case, staples can be delivered through the adjunct and tissue after placement of the adjunct at the tissue treatment site.

13 Claims, 16 Drawing Sheets

(51) Int. Cl.
*A61B 17/00* (2006.01)
*A61M 35/00* (2006.01)

(56) References Cited

U.S. PATENT DOCUMENTS

| | | | |
|---|---|---|---|
| 8,393,514 B2 | 3/2013 | Shelton, IV et al. | |
| 9,282,962 B2 | 3/2016 | Schmid et al. | |
| 2002/0122944 A1* | 9/2002 | Ogle | A61L 24/046 428/413 |
| 2005/0021026 A1 | 1/2005 | Baily | |
| 2005/0245966 A1* | 11/2005 | Hammerslag | A61L 24/001 606/214 |
| 2009/0255978 A1* | 10/2009 | Viola | A61B 17/0644 227/180.1 |
| 2010/0081617 A1* | 4/2010 | Okano | A61K 9/0004 514/18.2 |
| 2012/0209319 A1* | 8/2012 | Bianco-Peled | A61L 24/001 606/213 |
| 2013/0221065 A1 | 8/2013 | Aronhalt et al. | |
| 2013/0256377 A1 | 10/2013 | Schmid et al. | |
| 2015/0129634 A1 | 5/2015 | Shelton, IV et al. | |
| 2015/0133995 A1 | 5/2015 | Shelton, IV et al. | |
| 2015/0133996 A1 | 5/2015 | Shelton, IV et al. | |
| 2015/0134076 A1 | 5/2015 | Shelton, IV et al. | |
| 2015/0134077 A1 | 5/2015 | Shelton, IV et al. | |
| 2015/0272575 A1 | 10/2015 | Leimbach et al. | |
| 2015/0277471 A1 | 10/2015 | Leimbach et al. | |
| 2015/0351753 A1 | 12/2015 | Shelton, IV et al. | |
| 2015/0351758 A1 | 12/2015 | Shelton, IV et al. | |
| 2016/0015373 A1* | 1/2016 | Russo | A61B 17/00491 604/290 |
| 2016/0089142 A1 | 3/2016 | Harris et al. | |
| 2017/0055986 A1 | 3/2017 | Harris et al. | |

FOREIGN PATENT DOCUMENTS

| | | |
|---|---|---|
| EP | 2837337 A1 | 2/2015 |
| WO | WO-2015157459 A1 | 10/2015 |

* cited by examiner

METHODS AND DEVICES FOR DELIVERING AND SECURING ADJUNCT MATERIALS TO A TREATMENT SITE

FIELD

Methods and devices are provided for delivering and securing adjunct materials to treatment sites.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

While surgical staplers have improved over the years, a number of problems still present themselves. One common problem is that leaks can occur due to the holes formed when staples penetrate the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein. It can also be recognized that there may be a need in certain surgical circumstances to reinforce tissue, such as when trauma has occurred, to return the tissue as much as possible to its natural characteristics by delivering and securing adjunct materials to the treatment site.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

Methods and devices are provided for delivering and securing adjunct materials to treatment sites. In one embodiment, a method for stapling tissue is provided and includes activating an applicator to deliver a flowable adjunct precursor to a tissue with the applicator and, after the flowable adjunct precursor solidifies to form an adjunct, delivering at least one staple through the adjunct and the tissue.

The flowable adjunct precursor can be delivered using a variety of techniques. In one embodiment, the applicator can include a tubular shaft in fluid communication with a reservoir containing the flowable adjunct precursor. In another embodiment, the applicator can include a brush that contains the adjunct precursor.

In another aspect, the method can include causing the adjunct precursor to solidify after activating the applicator and before delivering at least one staple. Solidifying the adjunct precursor can include at least one of moistening the adjunct precursor, heating the adjunct precursor, cooling the adjunct precursor, exposing the adjunct precursor to light energy, applying a co-reactant to the adjunct precursor, and waiting a selected time duration.

The adjunct precursor can be applied to various locations of the tissue. In one embodiment, the adjunct precursor can be applied to opposed sides of the tissue at approximately the same location. In another embodiment, the adjunct precursor can be applied to a first side of the tissue and the method can further include applying a solid adjunct, different from the adjunct precursor, to a second side of the tissue.

In a further aspect, the method can include applying a mesh including a co-reactant over the adjunct precursor applied to the tissue prior to solidification. The co-reactant can be configured to catalyze solidification of the adjunct precursor.

In another embodiment, an adjunct delivery device is provided and includes an elongate shaft having a non-stapling end effector with first and second jaws configured to grasp tissue therebetween and an adjunct positioned on the first jaw and configured to be released from the first jaw when the tissue is engaged between the first and second jaws.

The first and second jaws can have a variety of configurations. In one embodiment, the first and second jaws can include approximately flat tissue contacting surfaces. In another embodiment, the first jaw can include a plurality of barbed pins configured to engage the adjunct.

The adjunct can have a variety of configurations. In one embodiment, the adjunct can be hinged such that a first portion of the adjunct is retained on the first jaw and a second portion of the adjunct is retained on the second jaw. In another embodiment, lateral edges of the adjunct can include flanges extending towards the first jaw.

In a further embodiment, a surgical stapling device is provided and includes an elongate shaft having an end effector with first and second jaws configured to grasp tissue therebetween. The first jaw can have a cartridge containing a plurality of staples and an adjunct mounted thereon, and the second jaw can have a sheet of material disposed thereon. The first jaw can be configured to release the adjunct on a first side of the tissue and the second jaw can be configured to release the sheet of material on a second side of the tissue opposite the adjunct.

In another aspect, the end effector can be configured to fire a plurality of staples through the adjunct to cause the adjunct to be released from the end effector. As an example, the plurality of staples can fix the adjunct to the tissue surface, thus aiding the adjunct to be released from the end effector.

BRIEF DESCRIPTION OF DRAWINGS

This invention will be more fully understood from the following detailed description taken in conjunction with the accompanying drawings, in which.

DETAILED DESCRIPTION

Figure 1:
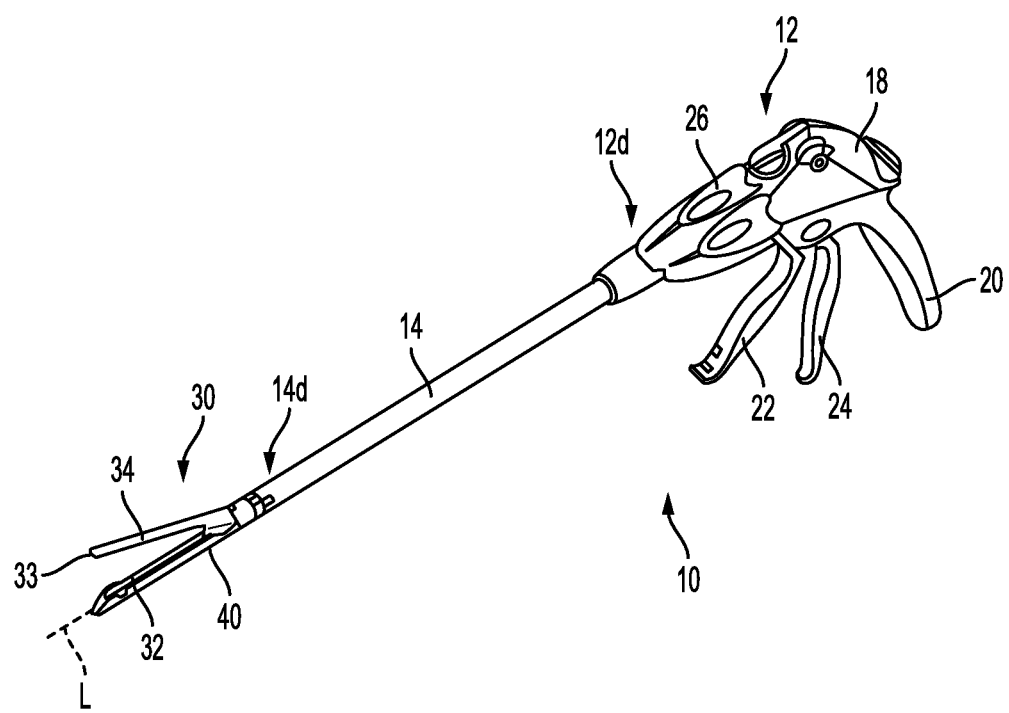
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It can be desirable to use one or more biologic materials and/or synthetic materials, collectively referred to herein as "adjuncts," in conjunction with surgical instruments to help improve surgical procedures. In general, when using an adjunct in conjunction with a surgical stapler, the adjunct can be removably attached to the end effector of the surgical stapler. The adjunct will preferably remain secured to the end effector while the end effector is positioned at a treatment site, and is released from the end effector when staples are deployed at the treatment site to facilitate healing. However, it has been observed that adjuncts can prematurely detach from the end effector prior to staple deployment. Detachment of the adjunct from the end effector can occur in various forms, depending on the manner in which the end effector is used. For example, detachment can include vertical lift off of the adjunct from the end effector, lateral sliding of the adjunct with respect to the end effector, and/or curling of the edges of the adjunct from the surface of the end effector. Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

Various exemplary devices and methods are provided for placing an adjunct at a tissue treatment site prior to delivering staples through the tissue and adjunct. In one embodiment, a flowable adjunct precursor can be deposited on the surface of the tissue at the tissue treatment site. The flowable adjunct precursor can be configured to solidify after deposition to form an adjunct. In another embodiment, an adjunct delivery device can deliver a solid adjunct to the tissue treatment site. Staples can be delivered through the adjunct and tissue to thereby staple the tissue.

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife blade or other cutting element capable of creating a cut inside of the rows of staples to define an opening through tissue held within the jaws. The staplers can be used in a variety of different surgical procedures on a variety of tissues in a variety of different surgical procedures, for example in thoracic surgery or in gastric surgery.

Figure 2:
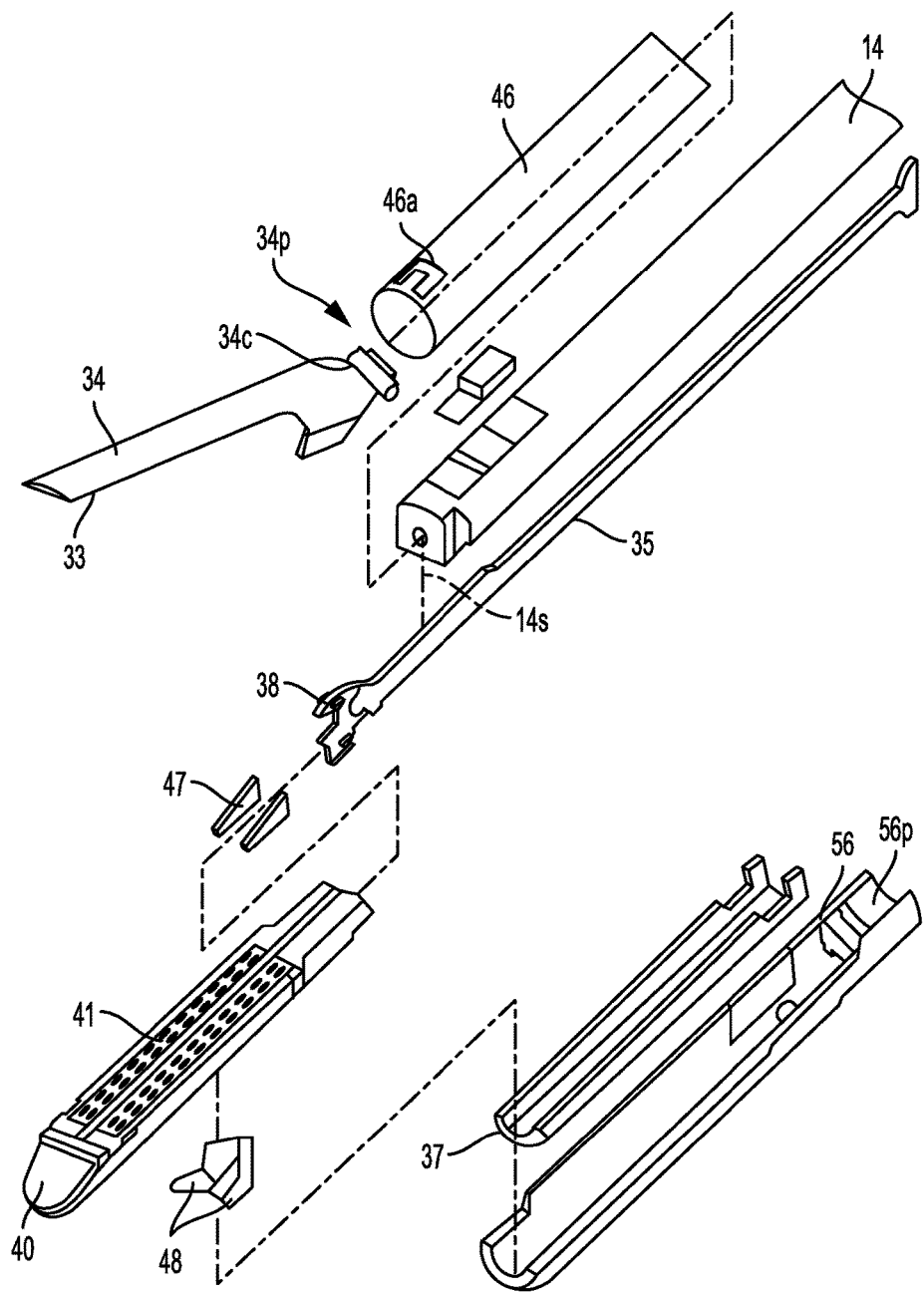
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil or tissue contacting surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple receiving cavities (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple receiving cavities formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
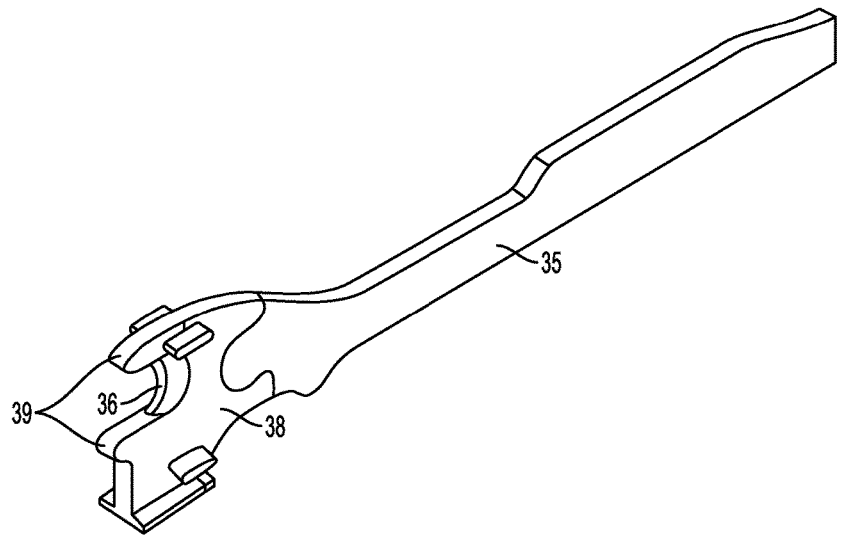
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through pockets 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the lower and upper jaws 32, 34 to compress the jaws 32, 34 toward one another as the firing bar 35 advances through the end effector 30. Simultaneously, the knife blade 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32,34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
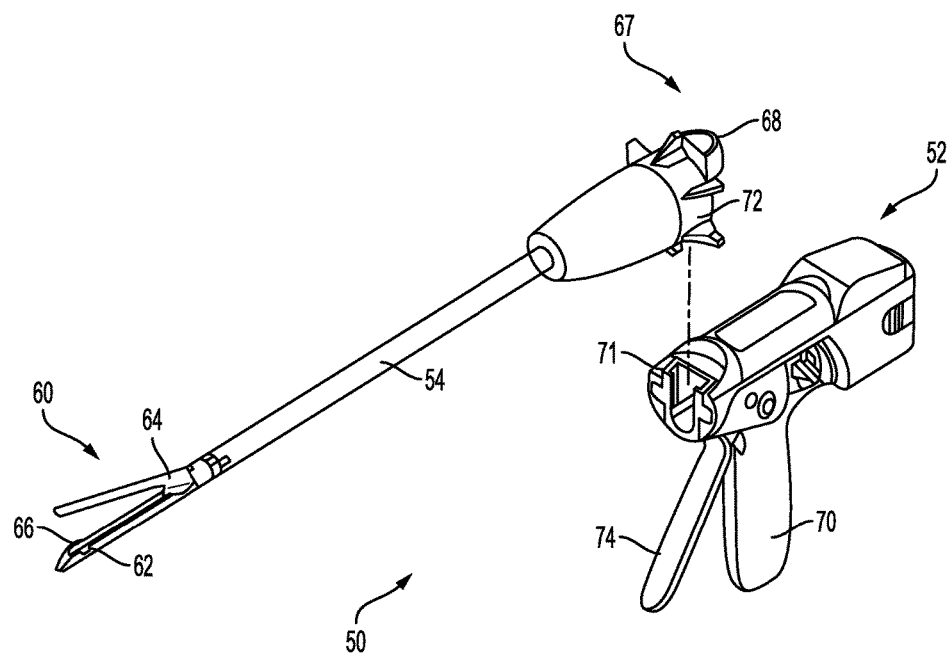
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 64 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

In further embodiments, the surgical instrument can adopt other forms. In one example, the surgical instrument is in the form of a circular surgical stapler (not shown). The circular stapler can generally be configured and used similarly to the linear staplers 10, 50 of FIGS. 1 and 4, but with some features accommodating its functionality as a circular stapler, such as a cartridge assembly configured to deploy staples against a circular anvil to form a circular pattern of staples, e.g., staple around a circumference of a tubular body organ.

The illustrated examples of surgical stapling instruments 10, 50 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures", and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a flowable liquid, a film, a laminate, a foam, an injection molded thermoplastic, a vacuum thermoformed material, a fibrous structure, and hybrids thereof. The adjunct can also include one or more biologically-derived materials, and/or synthetic materials, and/or one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct. The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S. L.)), hemostatic agents, and tissue healing agents.

The adjuncts can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. Pat. App. No. 14/840,613 entitled "Medicant Eluting Adjuncts and Methods of Using Medicant Eluting Adjuncts" and filed Aug. 31, 2015, which is hereby incorporated by reference in its entirety.

The adjunct can also be formed from flowable liquids made from a biocompatible and bioabsorbable material that can be configured to transition from a first liquid state to a second, hardened state (e.g., a sealant and/or adhesive). Examples of various sealants are further described in U.S. Patent Pub. No. 2015/0351753 entitled "Methods And Devices For Reinforcing A Staple Line" and filed Jun. 10, 2014, which is hereby incorporated by reference in its entirety. The flowable liquids can have various formulations and differing viscosity and solidification (curing) behavior. In other examples, the adjunct can include one or more solid components contained within a solvent. Examples of the solid components can include, but are not limited to, polylactones, cellulose derivatives, polyethylene glycol (PEG), poly(N-vinyl pyrrolidone), block copolymers of poly(N-isopropylacrylamide) (PNIPAAm), oxygenized regenerated cellulose (ORC), polydioxanone (PDO), any absorbable suture materials, and combinations thereof. Examples of the solvent(s) can include, but are not limited to, cyclohexane, N-methyl-2-pyrolidone, and combinations thereof.

While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. The adjunct can aid in reducing bleeding at the treatment site, either by tamponade action or by providing a hemostatic effect. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s).

Adjunct Delivery

Figure 5A:
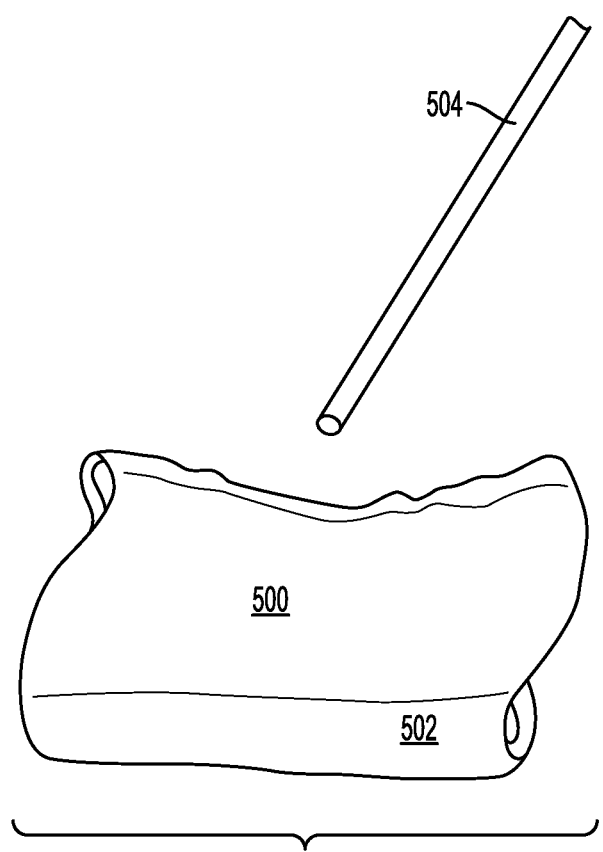
FIG. 5A is a perspective view of one embodiment of an applicator delivering a flowable adjunct precursor to a tissue.

FIG. 5A illustrates one embodiment for depositing a flowable adjunct precursor 500 upon a surface of a tissue 502 by an applicator 504. As shown, the applicator 504 is positioned adjacent to the tissue 502 and activated to cause the adjunct precursor 500 to flow from the applicator 504 to the tissue 502 for deposition at the treatment site. The viscosity of the adjunct precursor 500 can be low enough to facilitate flow from the applicator 504 to the tissue 502 and high enough to inhibit substantial flow once deposited upon the tissue 502. Additionally, the rheology of the adjunct precursor 500 can be selected to provide a shear thinning effect. As an example, the adjunct precursor 500 can exhibit a lower viscosity during application due the shear generated and exhibit a relatively higher viscosity once applied due to the near absence of shear.

The adjunct precursor 500 can be applied to one or more surfaces of the tissue 502. In one aspect, the adjunct precursor 500 can be applied to opposed surfaces of the tissue 502 at approximately the same location. In another aspect, not shown, the adjunct precursor 500 can be applied to a first surface of the tissue 502 and a solid adjunct, different from the adjunct precursor 500, can be applied to a second surface of the tissue 502 opposite the first surface of the tissue 502.

Figure 5B:
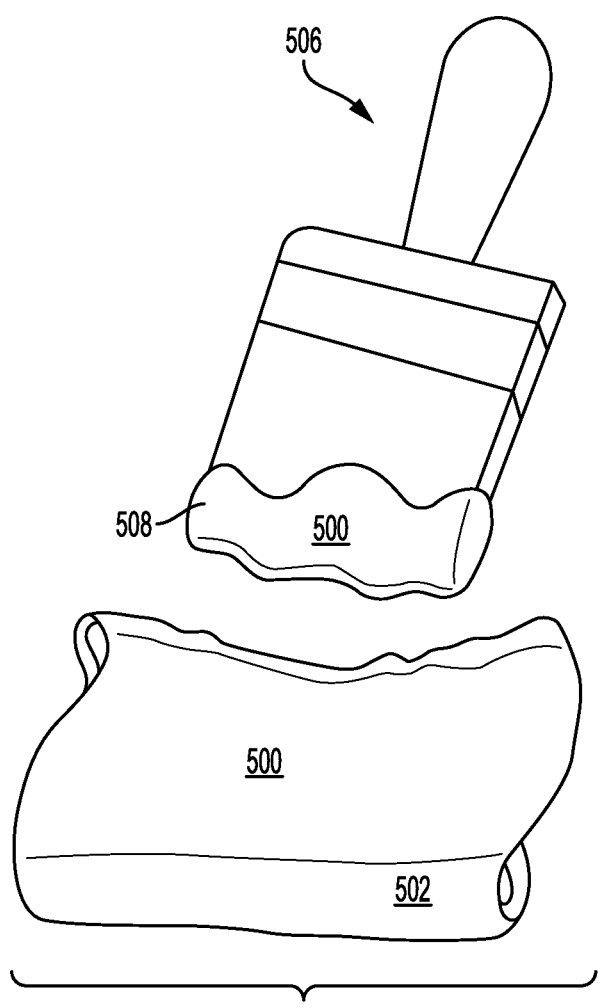
FIG. 5B is a perspective view of another embodiment of an applicator delivering a flowable adjunct precursor to a tissue.

Embodiments of the applicator 504 can take various forms. As illustrated in FIG. 5A, in one embodiment, the applicator 504 can include a tubular shaft in fluid communication with a reservoir (not shown) of the adjunct precursor 500. Under the influence of pressure, the adjunct precursor 500 is urged from a distal end of the applicator 504 and onto the surface of the tissue 502. A person skilled in the art will appreciate that the applicator can adopt other configurations suitable for deposition of the adjunct precursor 500 upon the tissue 502. As illustrated in FIG. 5B, in another embodiment, an applicator 506 can include a brush that contains the adjunct precursor 500 (e.g., within bristles 508 of the brush).

The adjunct precursor 500 can be configured to solidify after deposition upon the tissue 502 to form a solid adjunct. Solidification of the adjunct precursor 500 to form the solid adjunct can be accomplished using various techniques, such as moistening the adjunct precursor, heating or cooling the adjunct precursor, exposing the adjunct precursor to light energy, applying a hardener to the adjunct precursor, waiting a selected time duration after deposition, etc.

In one embodiment, the adjunct precursor 500 can be a biologically compatible heterogeneous mixture including one or more solid components and one or more solvents. The solvent(s) can evaporate over time due to body heat from the tissue 502 and/or externally supplied heat, forming the solid adjunct from the remaining solid components.

Figure 5C:
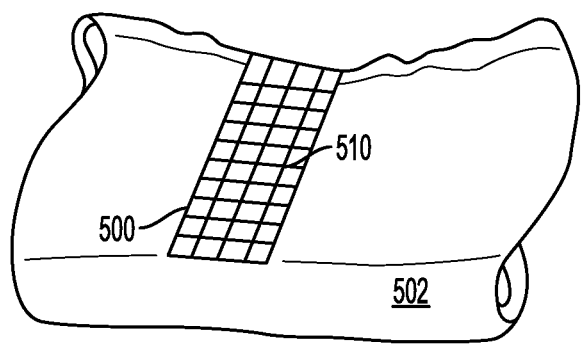
FIG. 5C is a perspective view of a mesh employed in combination with a flowable adjunct precursor delivered to a tissue.

In an alternative embodiment, the adjunct precursor 500 can be a biologically compatible chemical composition that solidifies (e.g., cures or hardens) after exposure to one or more of light energy (e.g., ultraviolet light), heat, or one or more co-reactants (e.g., catalysts, hardeners, etc.). Solidification of the chemical composition can take the form of cross-linking between components of the chemical composition or components of the chemical composition and co-reactants. Embodiments of the adjunct precursor 500 that are configured to solidify after exposure to one or more co-reactants can receive the co-reactants in a variety of ways. In one aspect, the co-reactant can be mixed with the adjunct precursor 500 at a selected time prior to deposition upon the tissue 502 (e.g., immediately prior to deposition). In another aspect, the co-reactant can be applied to the adjunct precursor 500 after deposition (e.g., by a dropper or sprayer). In a further aspect, the co-reactant can be transferred from the surface of an object to the adjunct precursor 500 by contact. For example, as shown in FIG. 5C, a mesh 510 including the co-reactant can be applied to the deposited adjunct precursor 500 prior to solidification (e.g., over the adjunct precursor 500 and/or embedded within the deposited adjunct precursor 500). The co-reactant can be positioned on the surface of the mesh 510 or contained within the mesh 510 and released upon contact with the adjunct precursor 500. Alternatively or additionally, at least a portion of the mesh 510 can be formed from the co-reactant. In further embodiments, the co-reactant can be provided in any combination of the above. Beneficially, use of the mesh 510 can provide further reinforcement to the solid precursor.

Figure 5D:
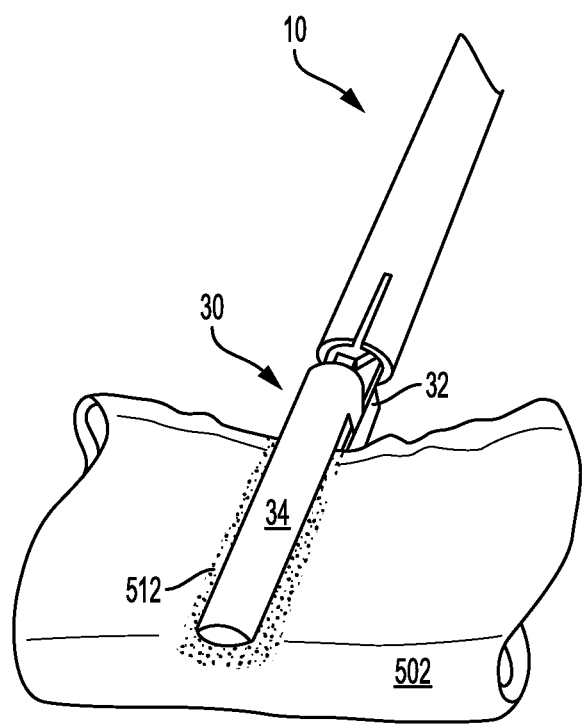
FIG. 5D is a perspective view of a stapler engaging tissue having an adjunct formed from any of the adjunct precursor of FIGS. 5A-5C.
Figure 5E:
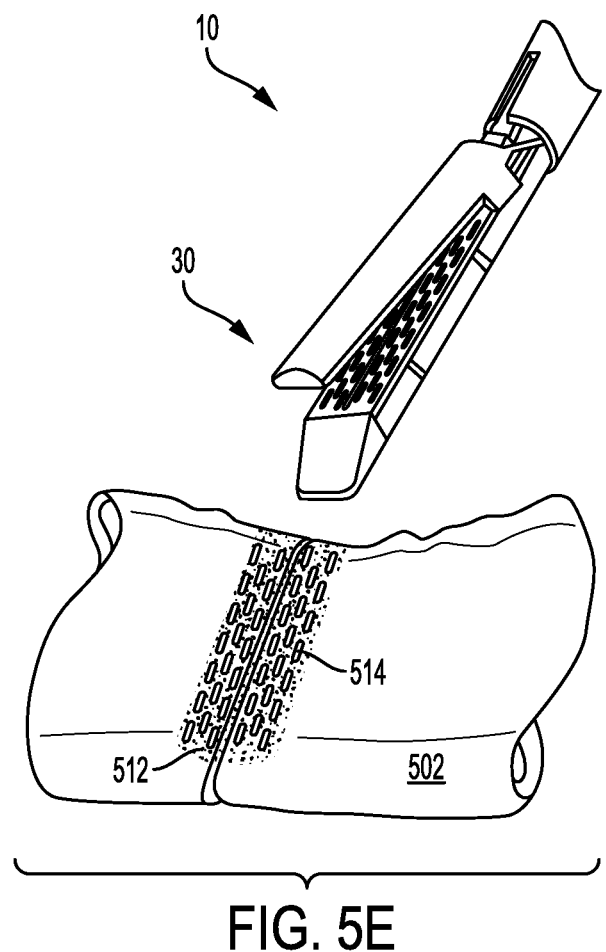
FIG. 5E is a perspective view illustrating the tissue and adjunct of FIG. 5D after delivery of a plurality of staples therethrough and the tissue is cut through the adjunct.

Following solidification of the adjunct precursor 500 to form the solid adjunct 512, one or more staples 514 can be delivered through the solid adjunct 512 and into the tissue 502. As illustrated in FIGS. 5D-5E, the end effector 30 of the stapler 10 can grasp the tissue 502 at the location of the solid adjunct 512 using the jaws 32, 34 and the firing system can be actuated to eject one or more staples 514 into the clamped tissue 502. As discussed above, the knife blade 36 (see FIG.

3) or other cutting element can be associated with the firing system to cut the tissue 502 during the stapling procedure, after tissue fixation has started.

Figure 6A:
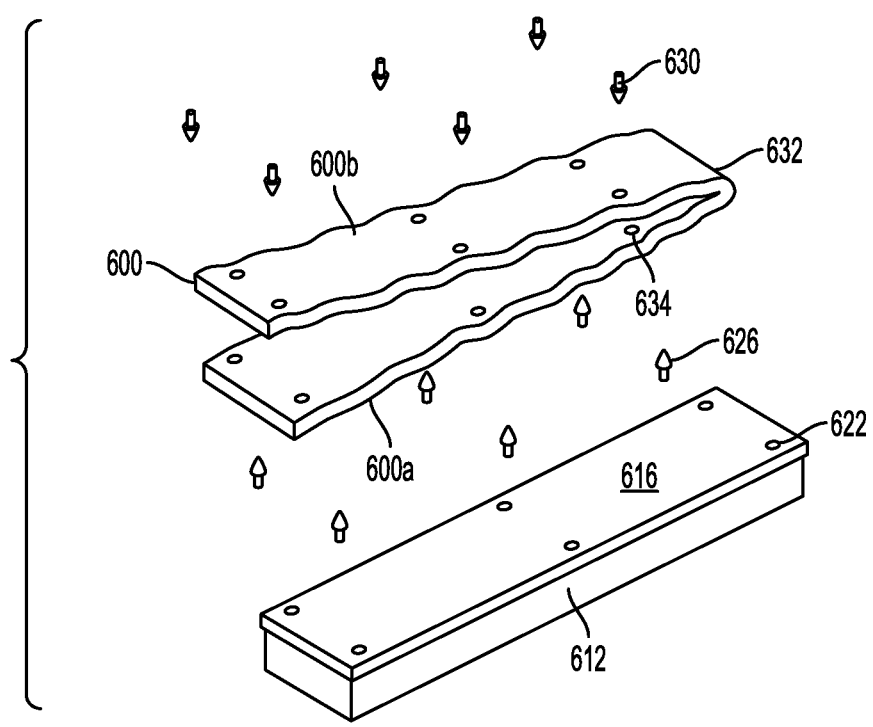
FIG. 6A is an expanded perspective view of another embodiment of an adjunct and a portion of an end effector of an adjunct delivery device configured to deliver the adjunct to a tissue treatment site.
Figure 6B:
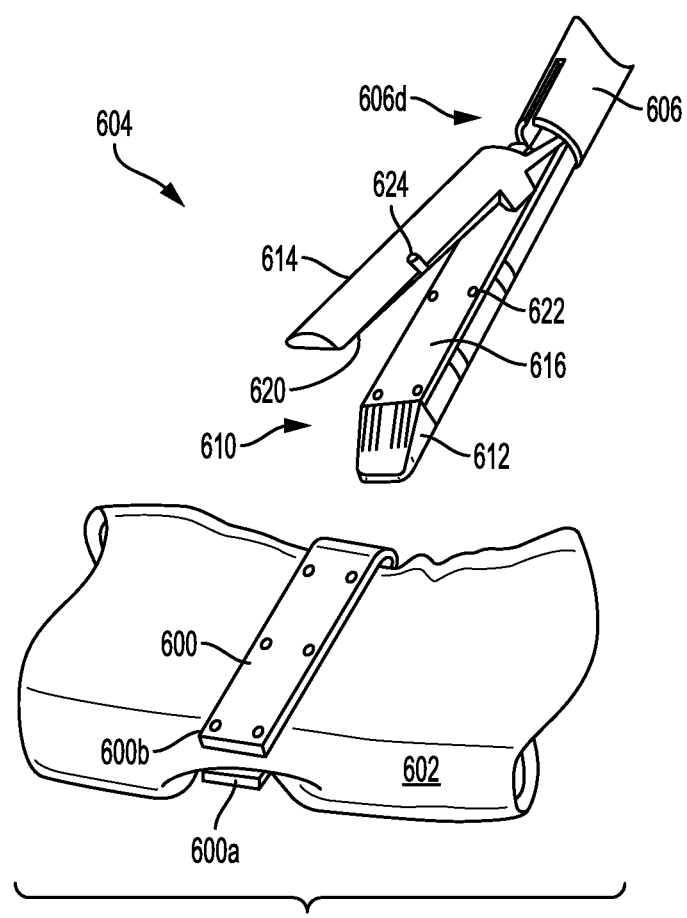
FIG. 6B is a perspective view of a tissue after deposition of the adjunct thereon by the adjunct delivery device of FIG. 6A.

FIGS. 6A-6B illustrate placement of another embodiment of an adjunct 600 upon a surface of a tissue 602 by an adjunct delivery device 604. The adjunct delivery device 604 can generally be configured and used similarly to the stapler 10 for grasping the tissue 602, except that the staple cartridge and firing system are omitted. As an example, the adjunct delivery device 604 can include an elongate shaft 606 having a non-stapling end effector 610 at a distal end 606d with opposed first and second jaws 612, 614 configured to grasp the tissue 602 therebetween. The adjunct delivery device 604 can further include a handle assembly (not shown) connected to a proximal end of the shaft 606 and configured to manipulate and operate the non-stapling end effector 610 similar to the handle assembly 12.

The non-stapling end effector 610 can be configured to secure the adjunct 600 thereon for placement of the adjunct 600 at a treatment site of the tissue 602 and to release the adjunct 600 when the tissue 602 is engaged by the non-stapling end effector 610. As illustrated in FIGS. 6A-6B, the first and second jaws 612, 614 can include approximately flat tissue contacting surfaces 616, 620 with a plurality of sockets 622, 624. The sockets 622, 624 are configured to receive corresponding barbed pins 626, 630. When the adjunct 600 is positioned on the tissue contacting surfaces 616, 620, the barbed pins 626, 630 extend through the adjunct 600, securing the adjunct 600 thereto by frictional engagement. After the adjunct 600 is positioned adjacent to the tissue 602, the jaws 612, 614 can be compressed to engage the tissue 602. The compressive force exerted by the jaws 612, 614 can drive a portion of the barbed pins 626, 630 into the tissue 602. Thus, when the jaws 612, 614 are retracted from the tissue 602, the barbed pins 626, 630 are retained in the tissue and the frictional engagement the barbed pins 626, 630 and the adjunct 600 retains the adjunct 600 in position on the tissue 602 prior to stapling.

As shown, the adjunct 600 can be formed from a single piece of material that includes a hinge 632. This hinged configuration can allow a first adjunct portion 600a on one side of the hinge 632 to be retained on the first jaw 612 by the barbed pins 626 and a second adjunct portion 600b on the other side of the hinge 632 to be retained on the second jaw 614 by the barbed pins 630. Beneficially, because the first and second adjunct portions 600a, 600b are connected by the hinge 632, the first and second adjunct portions 600a, 600b remain aligned when positioned on opposing sides of the tissue 602. The adjunct 600 and the barbed pins 626 can be formed from bioabsorbable materials, as discussed above, so that they are absorbed by the body during healing.

Optionally, the first and second adjunct portions 600a, 600b can include a plurality of holes 634 for receiving corresponding barbed pins 626, 630. The holes 634 can possess a diameter smaller than a diameter the barbed pins 626, 630 to facilitate frictional engagement of the adjunct 600 with the barbed pins 626, 630. Alternatively, the holes 634 can be omitted and the barbed pins 626, 630 can puncture the adjunct 600 for frictional engagement when positioned on the jaws 612, 614.

Figure 7A:
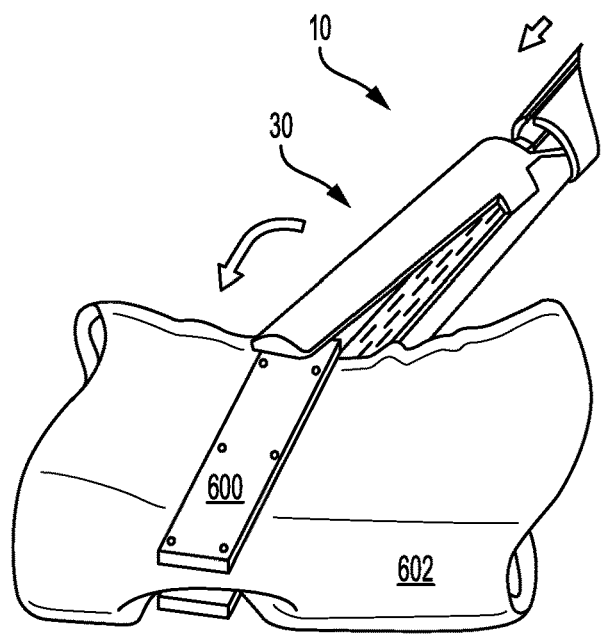
FIG. 7A is a perspective view of one embodiment of a stapler engaging the tissue and adjunct of FIG. 6B.
Figure 7B:
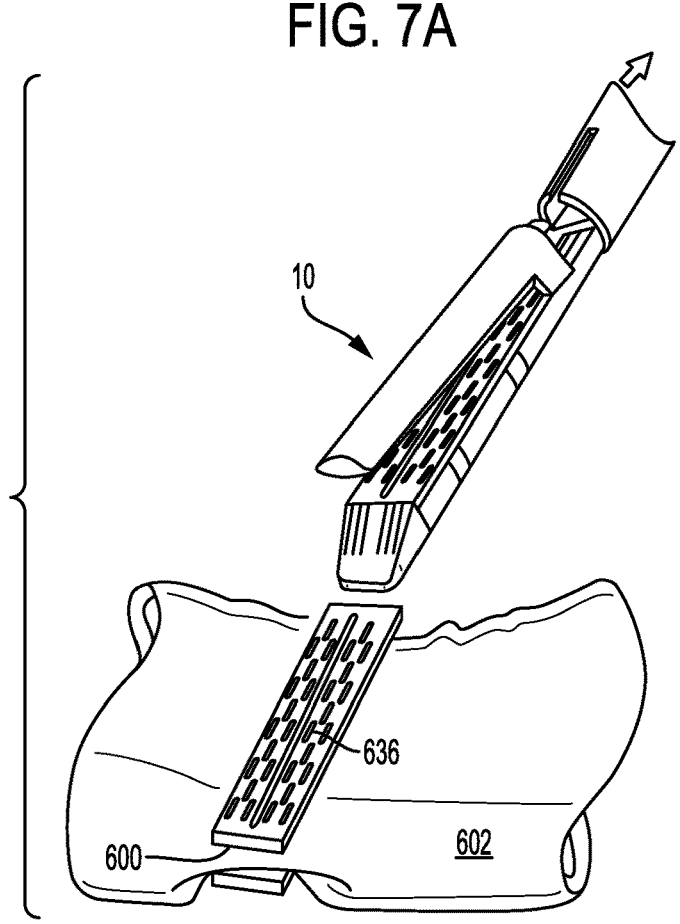
FIG. 7B is a perspective view of the tissue and adjunct of FIG. 6B after delivery of a plurality of staples therethrough.

Following placement of the adjunct 600 upon the tissue 602 by the adjunct delivery device 604, one or more staples 636 can be delivered through the adjunct 600 and into the tissue 602. As illustrated in FIGS. 7A-7B, the end effector 30 of the stapler 10 can grasp the tissue 602 at the location of the adjunct 600 using the jaws 32, 34 and the firing system can be actuated to eject one or more staples 636 into the clamped tissue 602. As discussed above, the knife blade 36 (see FIG. 3) or other cutting element can be associated with the firing system to cut the tissue 602 during the stapling procedure, after tissue fixation has started.

A person skilled in the art will appreciate that, while FIGS. 6A-7B illustrate the adjunct 600 as a generally planar structure including the hinge 632, the adjunct 600 can adopt any desired shape. In one example (not shown), the hinge 632 can be omitted and adjunct can be formed from two separate pieces that are secured to respective jaws 612, 614.

Figure 8A:
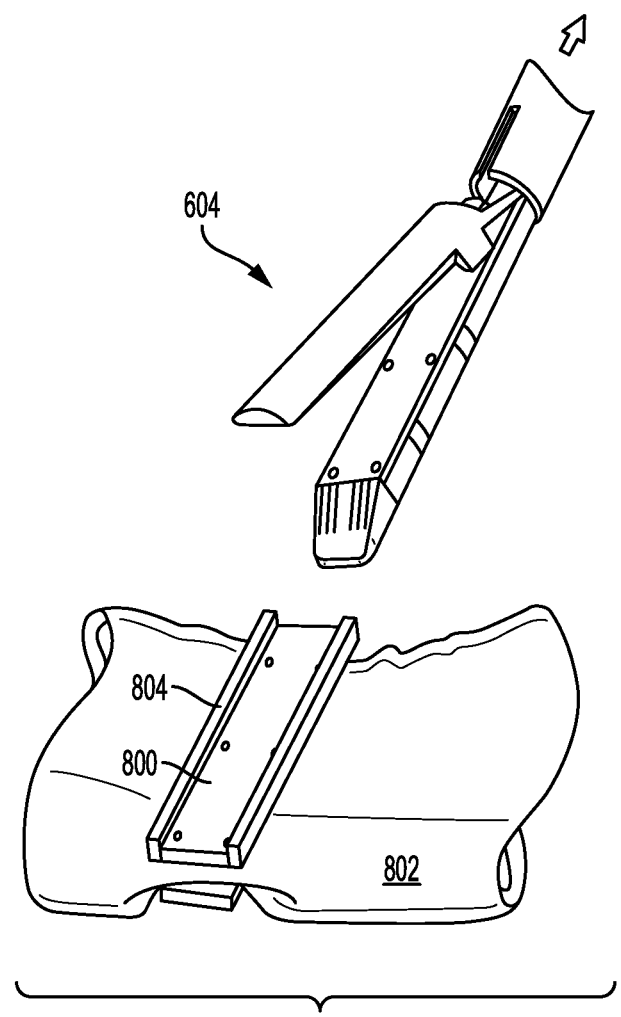
FIG. 8A is a perspective view of a tissue and an alternative embodiment of an adjunct including a plurality of lateral flanges configured to guide a stapler with respect to the adjunct.
Figure 8B:
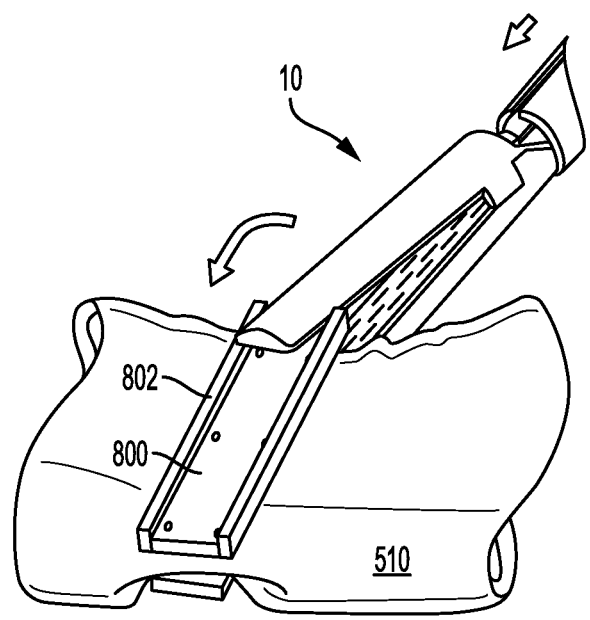
FIG. 8B is a perspective view of a stapler engaging the adjunct and the tissue of FIG. 8A.
Figure 8C:
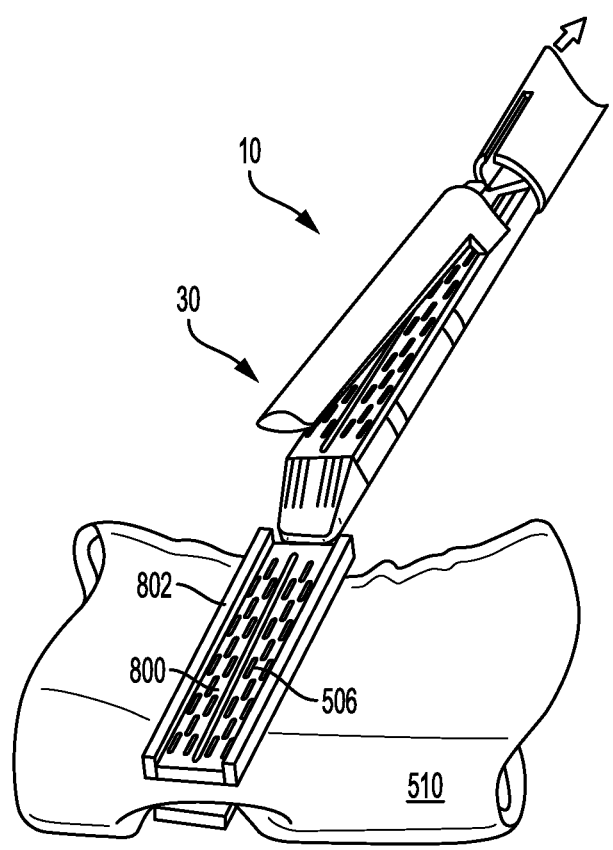
FIG. 8C is a perspective view the adjunct and tissue of FIG. 8B after delivery of the plurality of staples therethrough and the tissue is cut through the adjunct.

In another example, FIGS. 8A-8C illustrate a flanged adjunct 800 configured to be positioned on a tissue 802 by the adjunct delivery device 604. The flanged adjunct 800 includes flanges 804 along lateral edges that, when mounted on the adjunct delivery device 604, extend towards respective jaws 612, 614 upon which the flanged adjunct 800 is mounted. When positioned on the tissue 802, the flanges 804 can be dimensioned to facilitate alignment of a stapler 10 with the flanged adjunct 800 for delivery of one or more staples 806 through the flanged adjunct 800 and tissue 802. Optionally, the flanged adjunct 800 can be formed from a single, continuous piece with a hinge (not shown), as discussed above, to maintain alignment between respective portions of the flanged adjunct 800. In either instance, the flanged adjunct 800 can be delivered to tissue, and subsequently the flanges 804 can guide the jaws 612, 614 into alignment with the flanged adjunct 800 for staple delivery.

Figure 9A:
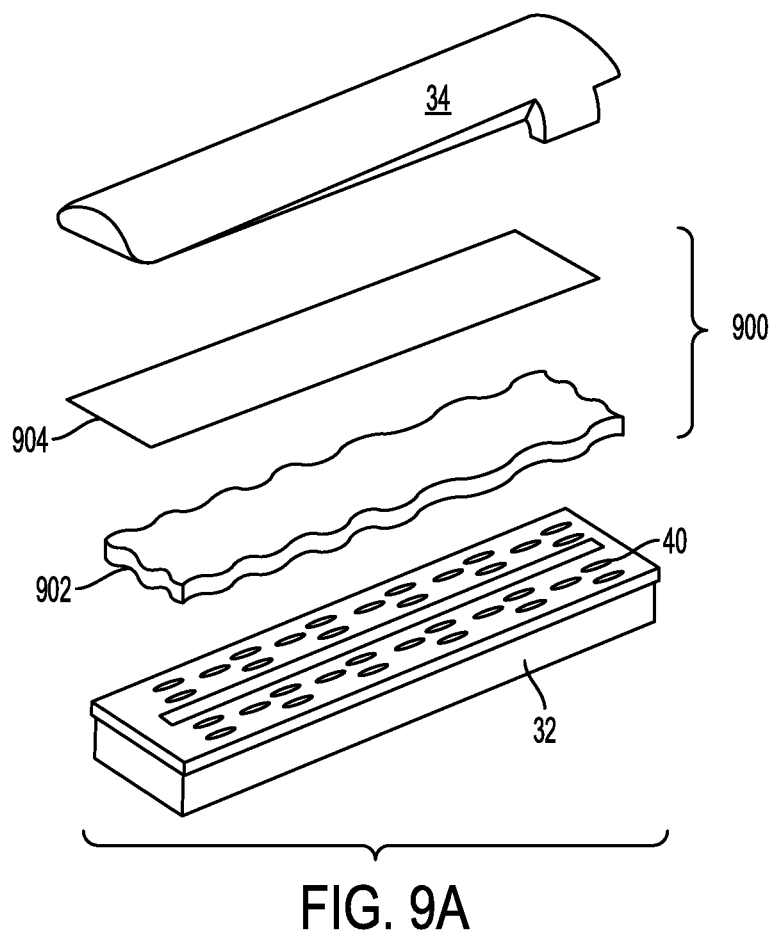
FIG. 9A is an expanded perspective view of another embodiment of an adjunct system configured for use with a surgical stapler.
Figure 9B:
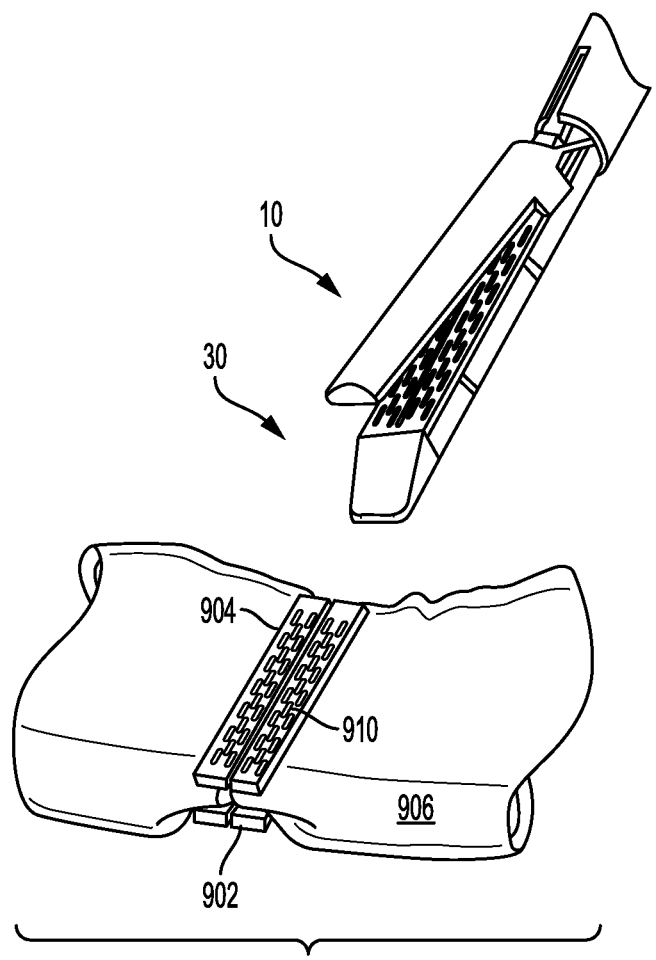
FIG. 9B is a perspective view of the adjunct system of FIG. 9A positioned on a tissue after delivery of a plurality of staples therethrough and the tissue is cut through the adjunct system.

Another embodiment of an adjunct system 900 configured for use with the stapler 10 is illustrated in FIGS. 9A-9B. The adjunct system 900 includes an adjunct 902 and a sheet of material 904, different from the adjunct 902. The adjunct 902 can be configured to be attached to the first jaw 32 including the staple cartridge 40 containing a plurality of staples and the sheet of material 904 can be configured to be attached to the second jaw 34. In certain embodiments, the adjunct 902 is only attached to the first jaw 32 and not the second jaw 34. The first and second jaws 32, 34 can include one or more attachment mechanisms for securing the adjunct 902 and the sheet of material 904 thereto. Examples of attachment mechanisms can include, but not limited to, adhesives, protrusions, etc. The strength with which the attachment mechanism secures the adjunct 902 and sheet of material 904 to respective jaws 32, 34 can be sufficient to retain adjunct 902 and sheet of material 904 thereon during placement of the adjunct system 900 on a tissue 906 and to release the adjunct 902 and the sheet of material 904 when staples are deployed through the adjunct 902. As an example, when the end effector 30 fires a plurality of staples 910 through the adjunct 902, the sheet of material 904, and the tissue 906, the staples 910 can secure the adjunct 902 to the tissue 906 with sufficient force to retain the adjunct 902 on the tissue 906 when the end effector 30 is retracted from the tissue 906 (FIG. 9B).

Terminology

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

A person skilled in the art will appreciate that the present invention has application in conventional minimally-invasive and open surgical instrumentation as well application in robotic-assisted surgery. In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

Reuse

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A method for stapling tissue, comprising:
activating an applicator to deliver a flowable adjunct precursor to a tissue within a body cavity with the applicator; and
after the flowable adjunct precursor solidifies to form an adjunct, engaging the tissue and the adjunct with opposed jaws on an end effector of a surgical stapling device, and actuating the surgical stapling device to deliver at least one staple through the adjunct and the tissue.

2. The method of claim 1, wherein the applicator comprises a tubular shaft in fluid communication with a reservoir containing the flowable adjunct precursor.

3. The method of claim 1, wherein the applicator comprises a brush that contains the adjunct precursor.

4. The method of claim 1, wherein the adjunct precursor is solidified by at least one of moistening the adjunct precursor, heating the adjunct precursor, cooling the adjunct precursor, exposing the adjunct precursor to light energy, applying a co-reactant to the adjunct precursor, and waiting a selected time duration.

5. The method of claim 1, wherein the adjunct precursor is applied to opposed sides of the tissue at approximately the same location.

6. The method of claim 1, wherein the adjunct precursor is applied to a first side of the tissue, and further comprising applying a solid adjunct, different from the adjunct precursor, to a second side of the tissue.

7. The method of claim 1, further comprising applying a mesh including a co-reactant over the adjunct precursor applied to the tissue prior to solidification.

8. The method of claim 7, wherein the co-reactant catalyzes solidification of the adjunct precursor.

9. The method of claim 1, wherein the flowable adjunct precursor is a biologically compatible heterogeneous mixture.

10. The method of claim 9, wherein the biologically compatible heterogeneous mixture includes one or more solid components and one or more solvents.

11. The method of claim 10, further comprising, after activating the applicator and before delivering the at least one staple, heating the adjunct precursor to cause the one or more solvents to substantially evaporate and solidify the adjunct precursor.

12. The method of claim 1, wherein the flowable adjunct precursor is a biologically compatible chemical composition.

13. The method of claim 12, further comprising at least one of heating the composition, exposing the composition to light energy, and applying one or more co-reactants to the composition.

* * * * *